(12) United States Patent
Stephan et al.

(10) Patent No.: US 10,130,588 B2
(45) Date of Patent: Nov. 20, 2018

(54) FUNCTIONALISED SILICON NANOPARTICLES

(71) Applicants: Westfaelische Wilhelms-Universitaet Muenster, Muenster (DE); Helmholtz-Zentrum Dresden-Rossendorf, Dresden (DE)

(72) Inventors: Holger Stephan, Dresden (DE); Ralf Bergmann, Dresden (DE); Alexander Ruffani, Heidenau (DE); Luisa DeCola, Strasbourg (FR)

(73) Assignee: WESTFAELISCHE WILHELMS-UNIVERSITAET MUENSTER, Munich (DE)

( * ) Notice: Subject to any disclaimer, the term of this patent is extended or adjusted under 35 U.S.C. 154(b) by 0 days.

(21) Appl. No.: 14/364,245

(22) PCT Filed: Dec. 12, 2012

(86) PCT No.: PCT/EP2012/075304
§ 371 (c)(1),
(2) Date: Jun. 10, 2014

(87) PCT Pub. No.: WO2013/087734
PCT Pub. Date: Jun. 20, 2013

(65) Prior Publication Data
US 2014/0377176 A1    Dec. 25, 2014

(30) Foreign Application Priority Data
Dec. 12, 2011 (GB) .................................. 1121288.3

(51) Int. Cl.
| | | |
|---|---|---|
| *A61K 9/51* | (2006.01) | |
| *C01B 33/02* | (2006.01) | |
| *C09C 1/28* | (2006.01) | |
| *C09C 1/30* | (2006.01) | |
| *C01B 33/027* | (2006.01) | |
| *A61K 49/00* | (2006.01) | |
| *A61K 51/12* | (2006.01) | |
| *B82Y 30/00* | (2011.01) | |
| *A61K 31/282* | (2006.01) | |
| *A61K 31/337* | (2006.01) | |
| *A61K 31/513* | (2006.01) | |
| *A61K 31/519* | (2006.01) | |
| *A61K 31/65* | (2006.01) | |
| *A61K 33/24* | (2006.01) | |
| *C07F 7/08* | (2006.01) | |
| *A61K 47/54* | (2017.01) | |
| *A61K 47/69* | (2017.01) | |

(52) U.S. Cl.
CPC .......... *A61K 9/5123* (2013.01); *A61K 31/282* (2013.01); *A61K 31/337* (2013.01); *A61K 31/513* (2013.01); *A61K 31/519* (2013.01); *A61K 31/65* (2013.01); *A61K 33/24* (2013.01); *A61K 47/54* (2017.08); *A61K 47/6923* (2017.08); *A61K 49/0093* (2013.01); *A61K 51/1244* (2013.01); *B82Y 30/00* (2013.01); *C01B 33/02* (2013.01); *C01B 33/027* (2013.01); *C07F 7/0827* (2013.01); *C09C 1/28* (2013.01); *C09C 1/3063* (2013.01); *C01P 2002/82* (2013.01); *C01P 2002/84* (2013.01); *C01P 2004/04* (2013.01); *C01P 2004/64* (2013.01); *C01P 2004/84* (2013.01); *C01P 2006/42* (2013.01); *Y10T 428/2982* (2015.01)

(58) Field of Classification Search
CPC combination set(s) only.
See application file for complete search history.

(56) References Cited

U.S. PATENT DOCUMENTS

| | | | | |
|---|---|---|---|---|
| 2007/0088414 | A1* | 4/2007 | Campbell et al. | ............ 607/101 |
| 2008/0102036 | A1* | 5/2008 | Poss et al. | ...................... 424/9.6 |
| 2013/0274226 | A1* | 10/2013 | Cheng | .............. A61K 47/48861 514/63 |

FOREIGN PATENT DOCUMENTS

| | | |
|---|---|---|
| CN | 101193962 A | 6/2008 |
| WO | 2006/076636 A1 | 7/2006 |

OTHER PUBLICATIONS

Shiohara et al: "Chemical Reactions on Surface Molecules Attached to Silicon Quantum Dots", Journal of the American Chemical Society, vol. 132, No. 1, Jan. 13, 2010 (Jan. 13, 2010), pp. 248-253.
Warner et al: "Water-Soluble Photoluminescent Silicon Quantum Dots", Angewandte Chemie. International Edition, VCH Verlag, Weinhejm, DE, vol. 44, No. 29, Jul. 18, 2005 (Jul. 18, 2005), pp. 4550-4554.
C Tu et. al: "PET imaging and biodistribution of silicon quantum dots in mice", ACS Med Chem Lett, vol. 2, No. 4, Jan. 2011 (2011-OJ), pp. 285-288.
Folarin Erogbogbo et al: "Biocompatible Luminescent Silicon Quantum Dots for Imaging of Cancer Cells", ACS Nano, vol. 2, No. 5, May 1, 2008 (May 1, 2008), pp. 873-878.
M. Rosso-Vasic et al: "alykl-Functionalized Oxide Free Silicon Nanoparticles: Synthesis and Optical Properties", Small, vol. 4, No. 10, 2008, pp. 1835-1841.
Shiohara, A., et al., "Sized controlled synthesis, purification, and cell studies with silicon quantum dots", Nanoscale, vol. 3, 2011, pp. 3364-3370.

(Continued)

*Primary Examiner* — Robert S Cabral
(74) *Attorney, Agent, or Firm* — 24IP Law Group; Timothy R DeWitt

(57) ABSTRACT

The present invention is related to silicon nanoparticles, a pharmaceutical composition comprising silicon nanoparticles, a method for synthesis of the silicon nanoparticles and their use for in vivo diagnostics, visualization of drug delivery or staining of cells, biological processes or pathways. The silicon nanoparticles are characterized that they comprise a silicon core of a size of 1 to 10 nm and are terminated with allylamine or poly(allylamine) comprising up to 10 allylamine groups.

22 Claims, 11 Drawing Sheets

(56) References Cited

OTHER PUBLICATIONS

Duan, X., et al., "Si Qdots: where does photoluminescence come from?", Self-Oganized Surfactant Structure (2011), pp. 135-144.

Rosso-Vasic, M., et. al., "Amine-terminated silicon nanoparticles: systhesis, optical properties and their use in bioimaging", Journal of Materials Chemistry, vol. 19, 2009, pp. 5926-5933.

Choi, J., et al.,"Conjugation of the Photoluminescent Silicon Nanoparticles to Streptavidin," Bioconjugate Chemistr;, vol. 19, 2008, pp. 680-685.

Wang, L., et al., "Silicon Nanoparticles as a Luminescent Label to DNA", Bioconjugate Chemistry, vol. 15, 2005, pp. 409-412.

Erogbogbo et al., "Biocompatible Luminescent Silicon Quantum Dots for Imaging of Cancer Cells," ACS Nano, 2 (5):873-8 (2008).

Erogbogbo et al., "Bioconjugation of luminescent silicon quantum dots for selective uptake by cancer cells," Bioconjug. Chem. Jun. 15, 2011;22(6):1081-8.

Fujioka et al, "Luminescent passive-oxidized silicon quantum dots as biological staining labels and their cytotoxicity effects at high concentration," Nanotechnology 2008;19(41):415102.

Rivolta et al., BONSAI Project Symposium; AIP Conference Proceedings 2010; 1275:94-97.

Amane Shiohara, et al., "Chemical Relations on surface molecules attached to silicon Quantum Dots," Journal of American Society, vol. 132, No. 1, pp. 248-253, published on Dec. 10, 2009.

Wang, X. et al.: "Exercited State Properties of Allylamine-Capped Silicon Quantum Dots", Journal of Physical Chemistry C. , vol. 111, No. 6, 2007, pp. 2394-2400.

\* cited by examiner

FUNCTIONALISED SILICON NANOPARTICLES

FIELD OF THE INVENTION

The present invention is related to silicon nanoparticles, a pharmaceutical composition comprising the silicon nanoparticles, a method for the synthesis of the silicon nanoparticles and their use for targeted in vivo diagnostics or drug delivery as well as visualization or staining of cells, biological processes or pathways.

BACKGROUND OF THE INVENTION

Digital imaging technologies have been used in various scientific fields for decades. As science develops, new instruments and techniques for imaging technologies are in great demand. Imaging technologies comprise optical/fluorescence imaging, x-ray imaging, magnetic resonance imaging (MRI), ultrasound, microwave, X-ray computed tomography (CT), positron emission tomography (PET) or single photon emission computed tomography (SPECT).

Bioimaging describes imaging technologies to study the integrative functions of biological molecules, cells, organ systems and whole organisms. Imaging technologies make use of molecular probes or interactions with molecules.

Advanced, multimodal imaging techniques, powered by new computational methods, are also available. These new imaging technologies allow examination of anatomical structures linked to functional data, as described by electric and magnetic fields, mechanical motion, and metabolism.

Bioimaging is useful for but not limited to in vivo diagnostics, visualization of drug delivery and cell staining. Biological pathways and processes can also be visualized.

Nanoparticles of uniform size and shape (preferably 3-5 nm diameter) have been proven an effective tool for bioimaging. Nanoparticles have a high area-to-volume ratio; they are very reactive, good catalysts and adhere to biological molecules. A preferred material is silicon as it is inert, non-toxic, abundant and economic. The silicon surface can be functionalized. Silicon nanoparticles show efficient photoluminescence in the visible part of the electromagnetic spectrum and are bioinert and chemically stable. The only material which has similar biocompatibility is porous silicon. Particles smaller than 100 nm show an enhanced permeability and retaining effect (EPR effect) in tumours, an important nonspecific targeting effect.

Silicon nanoparticles, also known as silicon quantum dots, can be used in imaging technologies but also for LED, photovoltaics, lithium ion batteries, transistors, polymers or two-photon absorption.

Efficient coupling of silicon nanoparticles to nucleotides has been shown by Wang et al. (Bioconjug. Chem. 2004; 15:409-12). Thereby nucleotides acquire a luminescent label. It has also been shown that silicon quantum dots can be coupled to streptavidin which retains their binding capability to biotin. Blue emission is retained in the silicon quantum dot-protein complex (Choi et al.: Bioconjug. Chem. 2008; 19:680-85).

Labelling of cancer cells has been described by Erogbogbo et al. (Bioconjug. Chem. 2011; 22(6):1081-8). Silicon quantum dots were conjugated to lysine, folic acid, antimesothelin or apo-transferrin for cellular labeling.

However, an important safety concern regarding toxicity of nanoparticles remains. Cytotoxicity and imaging properties of silicon quantum dots have been studied by Fujioka et al. They have shown efficient labeling of HeLa cells and less toxicity compared with cadium based quantum dots (Nanotechnology 2008; 19(41):415102).

Choi et al. have studied toxicity as well as inflammatory potential of silicon nanoparticles compared with silicon microparticles. While microparticles (10 to 3,000 nm) are less cytotoxic when compared at the same concentrations, silicon nanoparticles (3 nm) have shown a significantly lower cytotoxicity per particle. They also showed low inflammatory responses at high concentrations (Choi et al.: J. Appl. Toxicol. 2009; 29:52-60).

Despite numerous studies Rivolta et al. emphasize that silicon nanoparticles still need to reach a better stability in physiological media and more toxicity studies are necessary (BONSAI Project Symposium; AIP Conference Proceedings 2010; 1275:94-97).

Tu et al. studied biocompatibility and plasma clearance of dextran-coated $^{64}$Cu-DO3A conjugated silicon nanoparticles by PET. Both biocompatibility and plasma clearance are important parameters for clinical application. While the nanoparticles were also excreted from the body via renal filtration and urinary bladder, they mainly accumulated in the liver (ACS Med. Chem. Lett. 2011, 2:285-288).

BRIEF SUMMARY OF THE INVENTION

It is an objective of the present invention to provide low toxic and safe silicon nanoparticles which show fast distribution and fast clearance useful for high resolution imaging technologies. It is also intended to provide a method for manufacture of silicon nanoparticles and their use for targeted in vivo diagnostics, targeted in vivo therapy, visualization of drug delivery or staining of cells, biological processes or pathways.

The present disclosure provides silicon nanoparticles characterised in that they comprise a silicon core of a size of 1 to 10 nm and are terminated with allylamine or poly (allylamine) comprising up to 10 allylamine groups.

The nanoparticles can be mono-functionalised or multi-functionalised.

The functional group can be selected from the group comprising a luminescent compound, a fluorescent compound, a light absorbing compound, a radioactive compound, a metal compound that can be visualized using x-rays, a compound that can be visualized using magnetic resonance imaging (MRI), a compound that can be visualized using ultrasound or microwave, a luminescent/fluorescent material that can be utilized in optical imaging, a contrast-giving agent that can be imaged by X-ray computed tomography (CT) or an isotope that can be imaged by positron emission tomography (PET) or single photon emission computed tomography (SPECT).

Mono-functionalised within the meaning of the present disclosure means that one kind of functional group is bound to the surface of the nanoparticle. Thus, different functional groups of this one kind (e.g. different fluorescent compounds) or only one specific functional group (e.g. one specific fluorescent compound) is both possible. The amount bound is variable. It is possible that only a few of the respective functional groups are bound. It is also possible that the whole surface is saturated with the functional groups.

Multi-functionalised within the meaning of the present disclosure means that at least two different kinds of functional groups are bound to the surface of the nanoparticle. Again, only few functional groups can be bound or the whole surface can be saturated with functional groups. The proportion of each functional group is also variable and can be tuned by varying the concentrations of the different functional groups during the synthesis of the functionalised nanoparticles. The functional groups are thus added using a method allowing a directed attachment of more than one functional group.

The silicon nanoparticles may comprise at least the fluorescent compound Kodak X-Sight-670 and/or the radioactive compound $^{64}$Cu.

The nanoparticles can be bound to targeting molecules and/or therapeutically relevant molecules selected from the group comprising toxins, radionuclides and chemotherapeutics and the X-ray contrast-giving agents may comprise iodinated compounds or gadolinium based compounds.

The silicon nanoparticles may be bound to or comprise at least one biomolecule selected from the group comprising a peptide, a protein, a sugar molecule, a nucleic acid or nucleic acid analogue bound to the nanoparticle.

The protein may be an antigen, an antibody, a receptor or a ligand.

It is further intended that the nanoparticle is bound to at least one of proteins, lipids, surfactants, polymers encapsulating gas like perfluorpropane or sulphur hexafluoride.

The contrast-giving material comprises at least one paramagnetic material selected from the group comprising rare earth, gadolinium, manganese, iron and copper complexes and the contrast-giving agent for X-ray computed tomography may comprise barium salts and/or polyoxometalates.

For the PET nuclides it is intended that they may be selected from the group comprising $^{64}$Cu, $^{68}$Ga, $^{86}$Y, $^{89}$Zr, $^{110}$In or $^{18}$F based tracer and the SPECT nuclides may be selected from the group comprising $^{67}$Ga, $^{99m}$Tc, $^{111}$In or $^{201}$Tl.

A pharmaceutically active compound may be bound to the nanoparticle. A pharmaceutically active compound within the meaning of the present disclosure means any compound which brings about a pharmacological effect. The pharmacological effect can be a single effect, such as a cytostatic effect. The effect can also be a broad effect, such as the improvement of the immunological response towards pathogens.

The present disclosure also provides a pharmaceutical composition comprising silicon nanoparticles and a pharmaceutically suitable carrier. A pharmaceutically suitable carrier according to the present disclosure means any additive, excipient or encapsulating agent which is compatible with the nanoparticles and is not deleterious to the recipient. A pharmaceutically suitable carrier can be any organic or inorganic compound which can be co-administered with the nanoparticles to facilitate application.

A method for synthesis of the silicon nanoparticles is also provided. The method comprises the following steps: mixing a surfactant and a solvent and sonification of the mixture for forming micelles, adding $SiC_4$ and sonification, adding a reducing agent for forming hydrogen-terminated silicon nanoparticles and sonification, adding an allylamine or poly(allylamine) comprising up to 10 allylamine groups in the presence of a catalyst and sonification, and extracting and purifying the resulting silicon nanoparticles.

The sonification in each case can be performed simultaneously or subsequently to the respective step.

It is also intended that the method comprises tetraoctylammonium bromide as the surfactant, toluene as the solvent, LiAlH4 as the reducing agent and H2PtCl6 as the catalyst.

The nanoparticles can be used for bioimaging.

The pharmaceutical can also be used for bioimaging.

Bioimaging can be used for in vivo diagnostics, visualization or staining of drug delivery, of cells, biological processes or pathways.

The use of the described nanoparticles for chemotherapy, wherein a chemotherapeutic agent selected from the group comprising cisplatin, carboplatin, fluorouracil, methotrexate, paclitaxel, docetaxel or doxorubicin is bound to the nanoparticle is also provided.

The disclosed nanoparticles may also be used for radionuclide therapy, wherein a radio-metal complex is used comprising therapeutically relevant radionuclides selected from the group of $^{67}$Cu, $^{90}$Y, $^{131}$I, $^{153}$Sm, $^{166}$Ho, $^{177}$Lu, $^{186}$Re or $^{188}$Re.

The disclosed nanoparticle may also be used for a combination of molecular imaging and targeted treatment of diseases, wherein targeted treatment shall mean the treatment of specific cells or tissues as well as of specific pathways or molecular interactions like for instance blocking cell division or related pathways thereto.

BRIEF DESCRIPTION OF THE FIGURES

The disclosure will be illustrated by figures without being limited to them. It shows.

DETAILED DESCRIPTION OF THE INVENTION

Figure 1A:
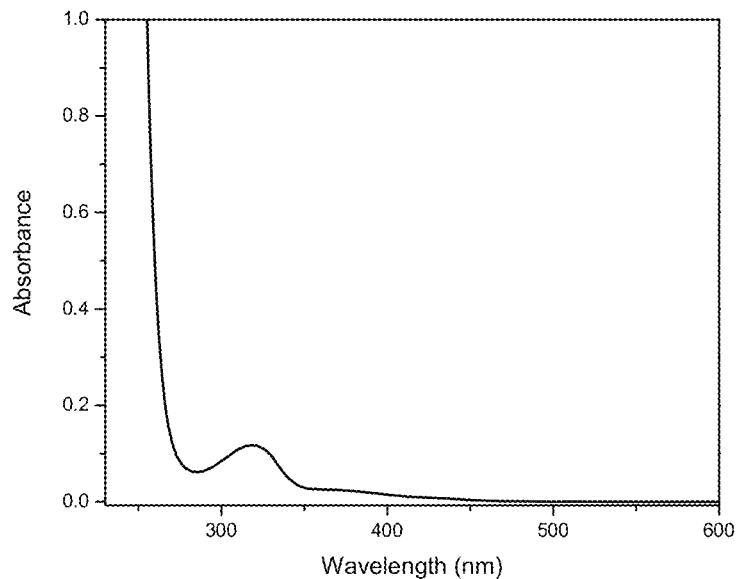
FIG. 1: 1A: Absorption spectrum of silicon nanoparticles. 1B: Emission spectra of silicon nanoparticles terminated with amino groups at different excitation wavelengths.

Functionalization is the addition of functional groups onto the surface of a material by chemical synthesis methods. The functional group added can be subjected to ordinary synthesis methods to attach virtually any kind of compound onto the surface. Silicon nanoparticles can be functionalised with a luminescent compound, a fluorescent compound, a light absorbing compound, a radioactive compound, a metal compound that can be visualized using x-rays, a compound that can be visualized using magnetic resonance imaging (MRI), a compound that can be visualized using ultrasound or microwave, an isotope that can be imaged by x-ray computed tomography (CT) or positron emission tomography (PET) or single photon emission computed tomography (SPECT). Multimodal imaging is also possible with the same strategy. Functionalization of silicon nanoparticles with therapeutic agents, e.g. toxins, radionuclides and chemotherapeutics will allow therapeutic applications.

Thus, particles can be functionalized with the relevant functional groups needed for a particular application, e.g. one group for targeting a special kind of tissue or cell and another groups as reporter group like a dye or a fluorescent compound or radiolabel or contrast-enhancing units.

Bioimaging within the meaning of the present disclosure means non-invasive labelling of biological structures such as biological molecules, whole cells or subcellular structures, organ systems, tissues such as tumour tissue or whole organisms. Biological pathways and processes can also be visualized.

Bioimaging is useful for but not limited to in vivo diagnostics, visualization of drug delivery and staining of cells, biological pathways and processes.

In vivo diagnostics within the meaning of the present disclosure comprises imaging technologies with the aim of labelling specific biological structures such as biological molecules, whole cells or subcellular structures, organ systems or tissues such as tumour tissue for diagnosis of diseases or disorders at a cellular level. For that purpose, contrast agents, antibodies or nanoparticles are exemplary molecules that are administered before or during examination.

Drug delivery comprises administering a pharmaceutical composition to achieve a therapeutic effect in humans or animals. Bioimaging can be useful in visualization of drug delivery in that pharmaceutical compositions are labeled as written above and administration is monitored via imaging technologies.

Cell staining can be performed in the same way. Whole cells or subcellular structures can be labeled as written above and visualized via imaging technologies.

Therapeutic treatment can be performed by combining the silicon nanoparticles modified with metal binding ligands with therapeutic radionuclides, toxins as well as chemotherapeutics, and administration in patients with tumours or other nanoparticles retaining foci of disease.

Targeting molecules shall comprise molecules directing the nanoparticles to specific cells, cell structures or tissues as well as molecules, which target for instance a specific cellular pathway and thus block tumour growth or spreading for example.

SYNTHESIS AND CHARACTERIZATION

Synthesis

Silicon nanoparticles were prepared using a modification of a method reported by Warner et al. 1.5 g of tetraoctylammonium bromide was mixed with 100 ml of dry toluene and mixture was sonicated for 30 min, in a $N_2$ glove box. 100 µl of $SiCl_4$ was added via a gas-tight syringe and sonication was continued for 30 min allowing entrance in micelles. Subsequently, 2.3 mL of $LiAlH_4$ (1 M in THF) was added in order to form hydrogen-terminated silicon nanoparticles. After 30 min of sonication, dry and deaerated methanol (30 ml) was added to react with the excess $LiAlH_4$.

Alkylamine terminated nanoparticles were obtained in the reactions of degassed allyl-amine (2.7 g), with hydrogen-terminated silicon nanoparticles, in the presence of 40 µl of 0.05 M $H_2PtCl_6$ catalyst. After 30 min of sonication, 3-amino-propyl silicon nanoparticles were extracted with water, washed with ethyl-acetate and filtrated twice through syringe membrane filters (Millex, Millipore, PVDF, 0.45 µm). The resulting silicon nanoparticles were further purified by dialysis against water (MWCO 7000, SERVA, Membra-Cel dialysis tubing, diameter 22 mm) to remove any residuals of unreacted amino-alkene and surfactant.

Silicon Nanoparticle Characterization

Figure 1B:
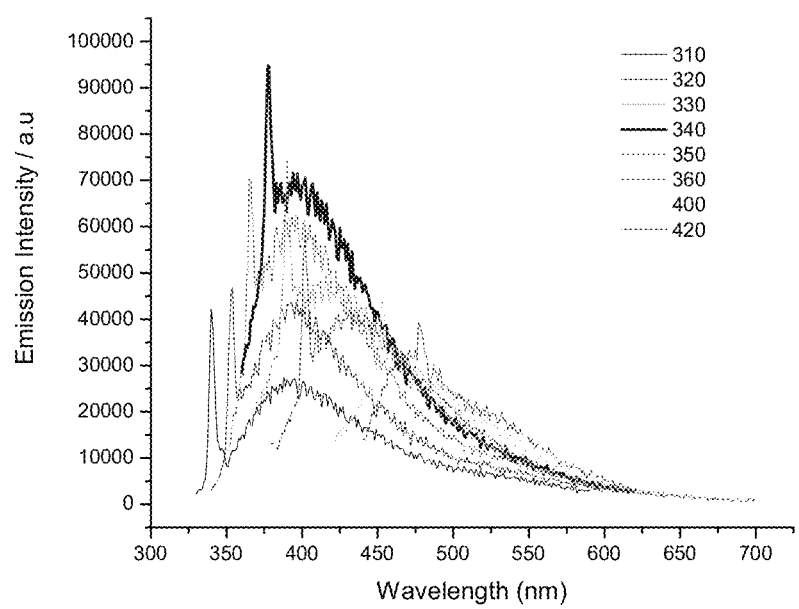
Figure 2A:
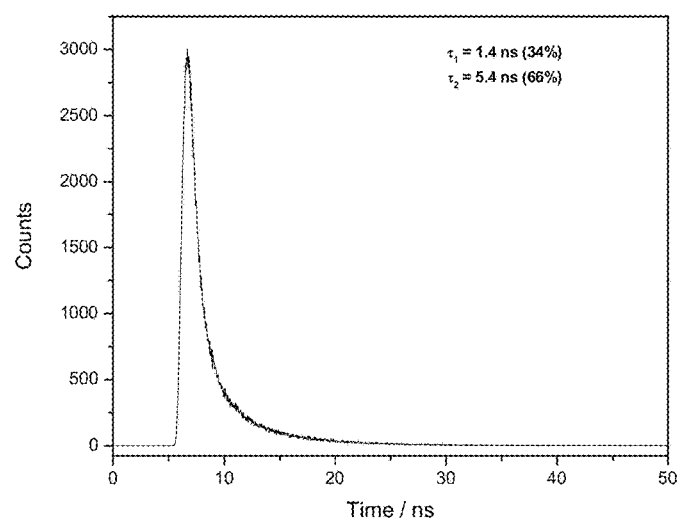
FIG. 2: 2A: Lifetime spectrum of silicon nanoparticles. 2B: FTIR spectrum of silicon nanoparticles.
Figure 2B:
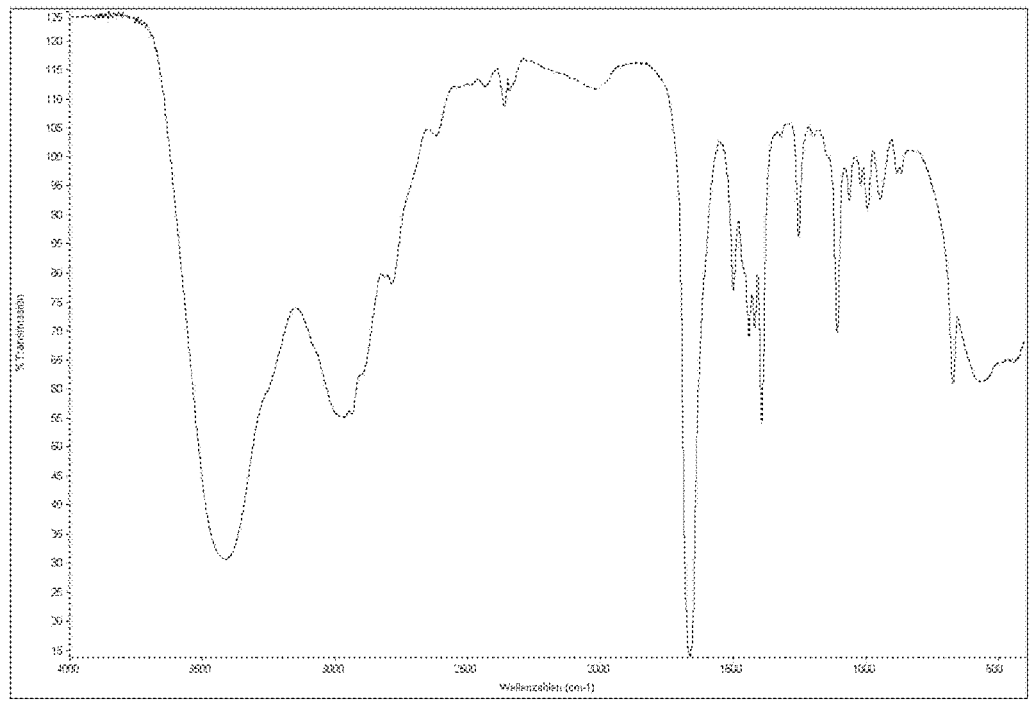

Characterization of these particles was done in collaboration with Dr. Manuel Tsotsalas. These include FTIR, NMR and HRTEM. In addition to this complete photophysical characterization was performed. These results are presented in FIG. 1 and FIG. 2.

These results confirm the formation of silicon nanoparticles. The 1661 $cm^{-1}$ in the IR data can be attributed to the allylamine vibrations and it clearly indicates attachment to the Si surface. The peaks between 1000 and 1100 $cm^{-1}$ can be attributed to Si—OR vibrations. These assignments are based on literature.

EXAMPLES

The disclosure will be illustrated by the following examples without being limited to them. The examples shown involve in vivo experiments.

Example 1: Preparation and In Vivo Characterization of Fluorophore-Labeled Silicon Nanoparticles (Kodak-Xs-670-Labeled Nanoparticles)

Figure 3:
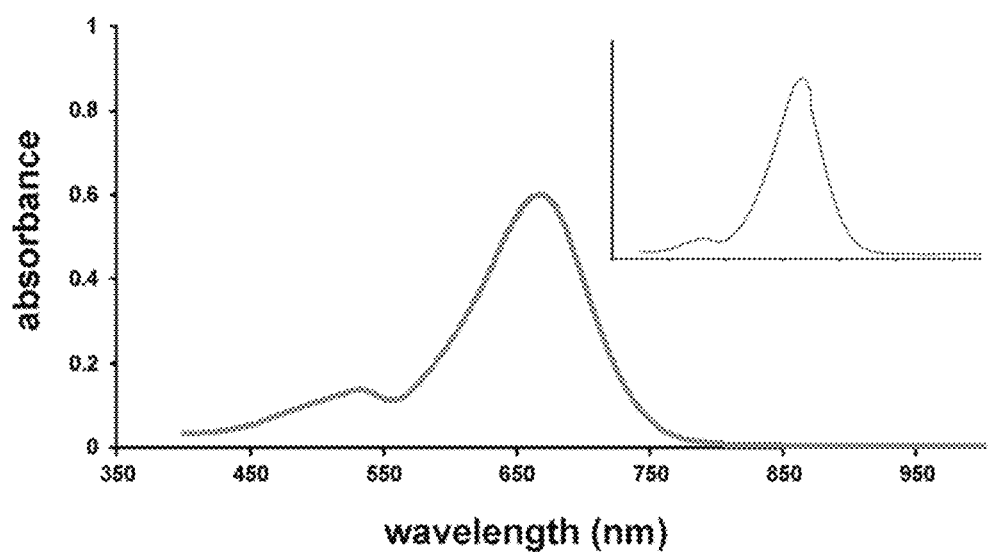
FIG. 3: Absorption spectra of Kodak-XS-670-labeled silicon nanoparticles and Kodak-XS-670 (inset) in water.
Figure 4:
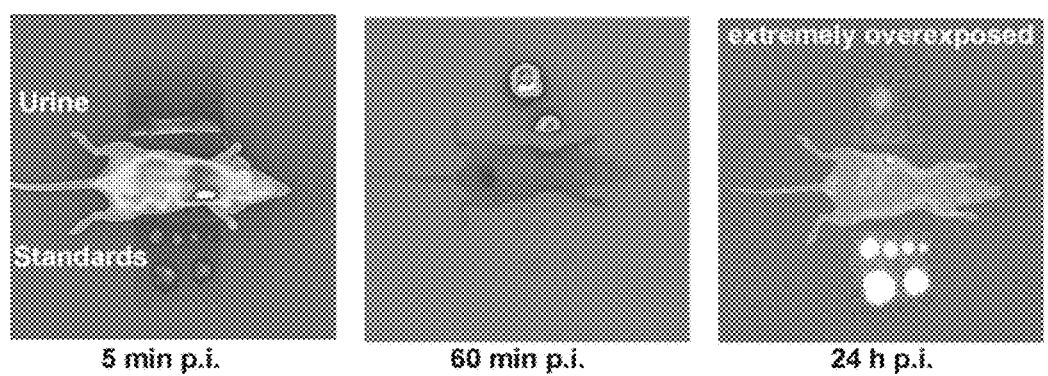
FIG. 4: In vivo fluorescence images of NMRI nu/nu mouse using Kodak-XS-670-labeled silicon nanoparticles (Kodak in vivo imaging system FX).
Figure 5:
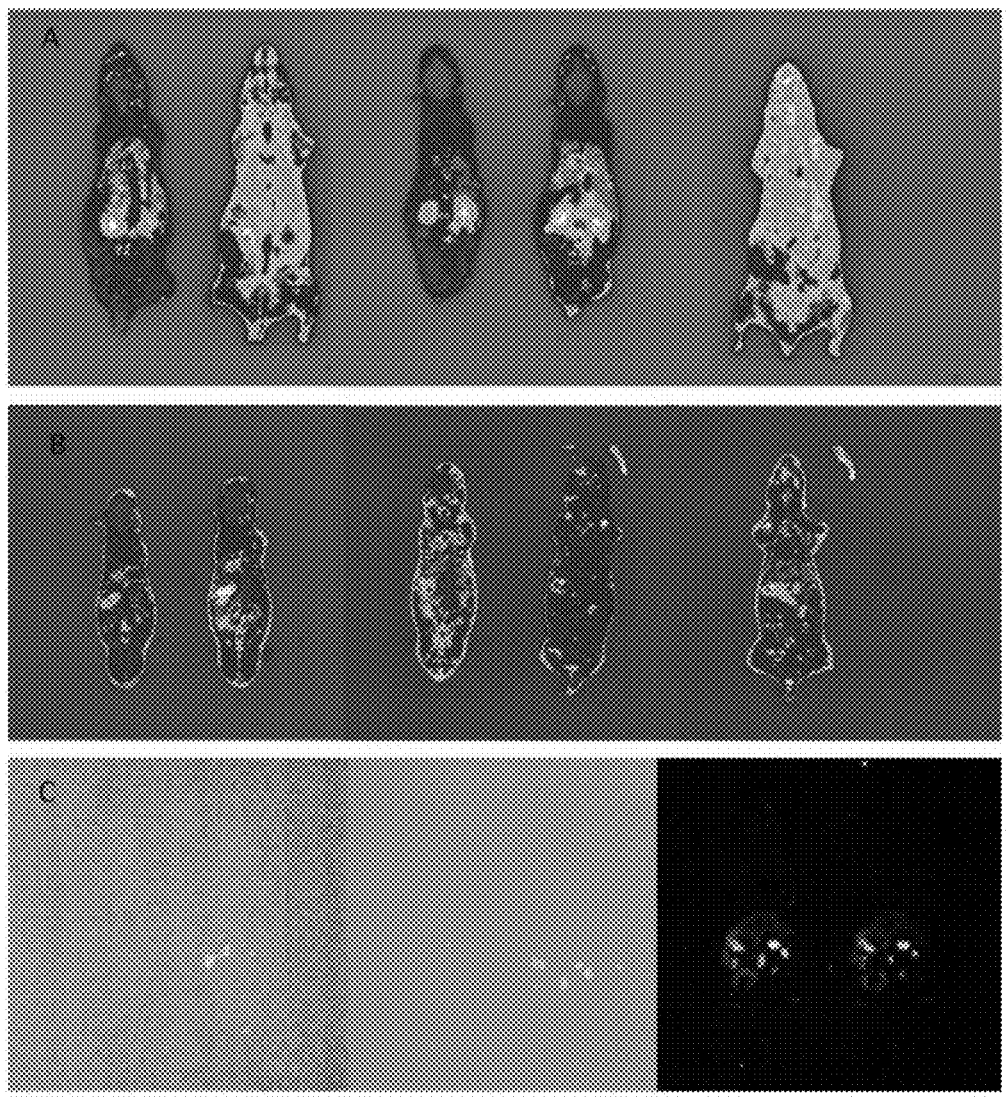
FIG. 5: Ex vivo whole body freeze section (80 µm) fluorescence images of NMRI nu/nu mice at 5 min (A), 60 min (B) and 24 h (C) after single intravenous injection of Kodak-XS-670-labeled silicon nanoparticles.

36 µL amino-terminated silicon nanoparticles (c=2 mg/mL) were added to 964 µL phosphate buffer (Sorensen, 10 mM, pH=7.5). Then, 1 mg (0.88 µmol) KODAK X-Sight-670 tetrafluorophenyl ester was added and the mixture was stirred for 3 hours at room temperature. Unreacted material was separated by dialysis (MWCO 7000, Serva, Membra-Cel) until the solvent becomes colorless (8 times with 300 mL $H_2O$ each in 8 hours cycles). 20 µL of XS-670-containing silicon nanoparticles were added to 680 µL $H_2O$ (c~0.025 mg/mL) and an absorption spectrum was recorded. As can be seen from FIG. 3, XS-670-containing silicon nanoparticles have the same absorption spectra as the free dye. An aqueous solution (~870 µg XS-670-Si-nanoparticles/mL) was used for in vivo experiments. In a typical experiment, 200 µL, of this solution was administered to a NMRI nu/nu mouse. In vivo fluorescence images of NMRI nu/nu mouse using Kodak-XS-670-labeled silicon nanoparticles were exposed with a Kodak in vivo imaging system FX after 5 minutes, 1 hour and 24 hours (FIG. 4). In parallel, ex vivo studies using frozen sections (80 µm thickness) of NMRI nu/nu mouse were performed with mice sacrificed after 5 min, 1 h or 24 h. The images (FIG. 5) show that the Kodak-XS-670-labeled nanoparticles were fast eliminated through the kidneys into the bladder. The particles were transiently observed in body regions with lymphatic system.

However, after 24 hours no fluorescence originating from the particles were detected in the body, exclusively in traces in the bladder.

Figure 6:
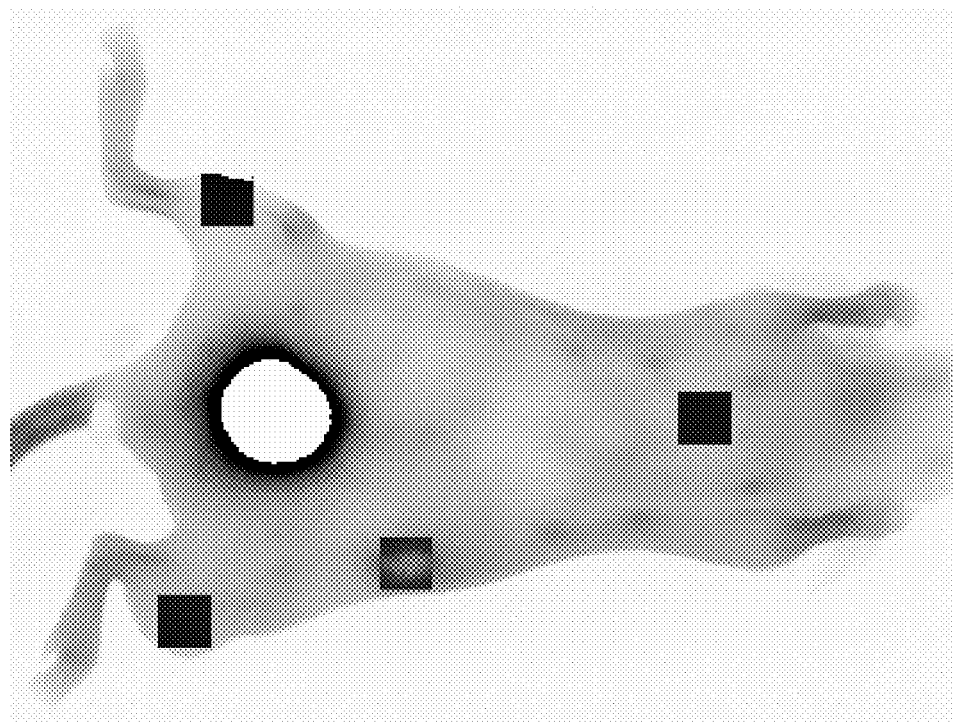
FIG. 6: Delineation of ROI's (bladder, heart, intestine, tumour, muscle) on a representative 2D fluorescence image of a nude mice after 2 h of single intravenous injection of 200 µL Kodak-XS-670-labeled silicon nanoparticles.
Figure 7:
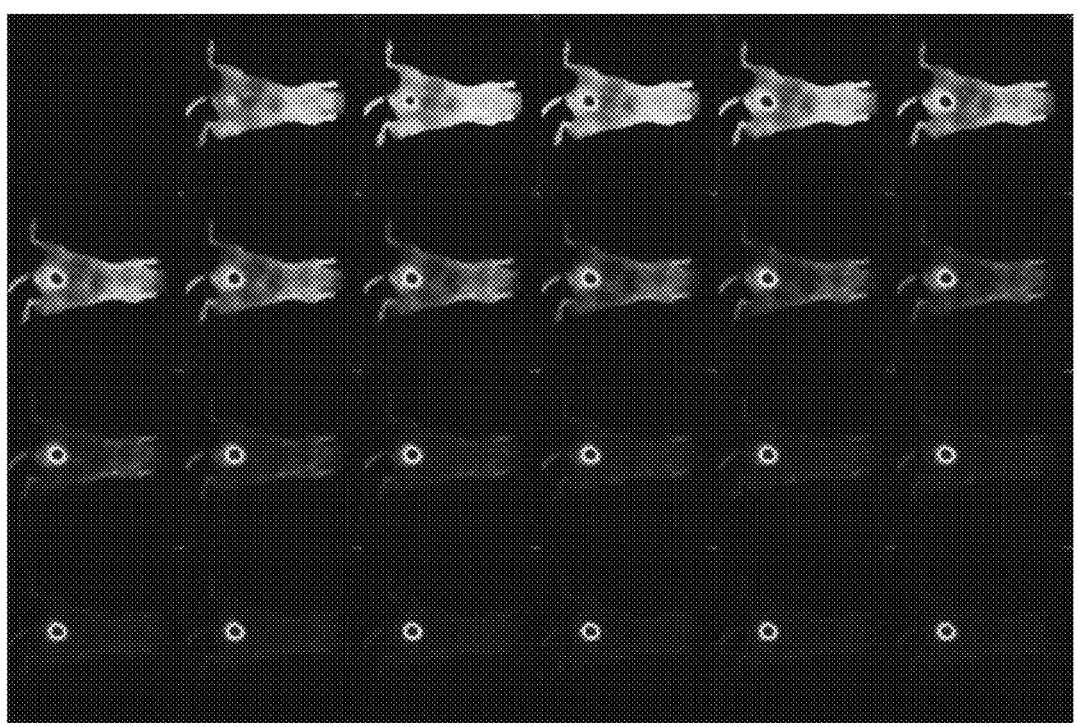
FIG. 7: 2D near infrared (NIR) fluorescence (excitation 670 nm, emission 790 nm, measurement duration of each frame 5 min) images measured before injection (0 min) of Kodak-XS-670-labeled silicon nanoparticles and every 5 min up to 2 hours.
Figure 8:
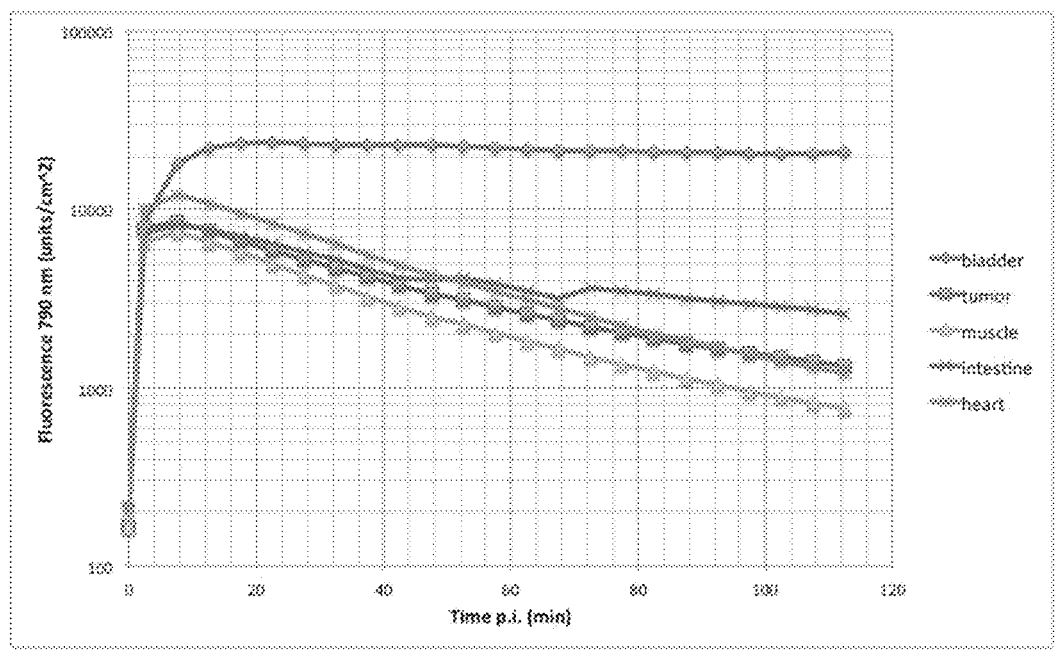
FIG. 8: Kinetics of the in vivo fluorescence intensity in ROIs of a representative mouse after single intravenous injection of Kodak-XS-670-labeled silicon nanoparticles.
Figure 9:
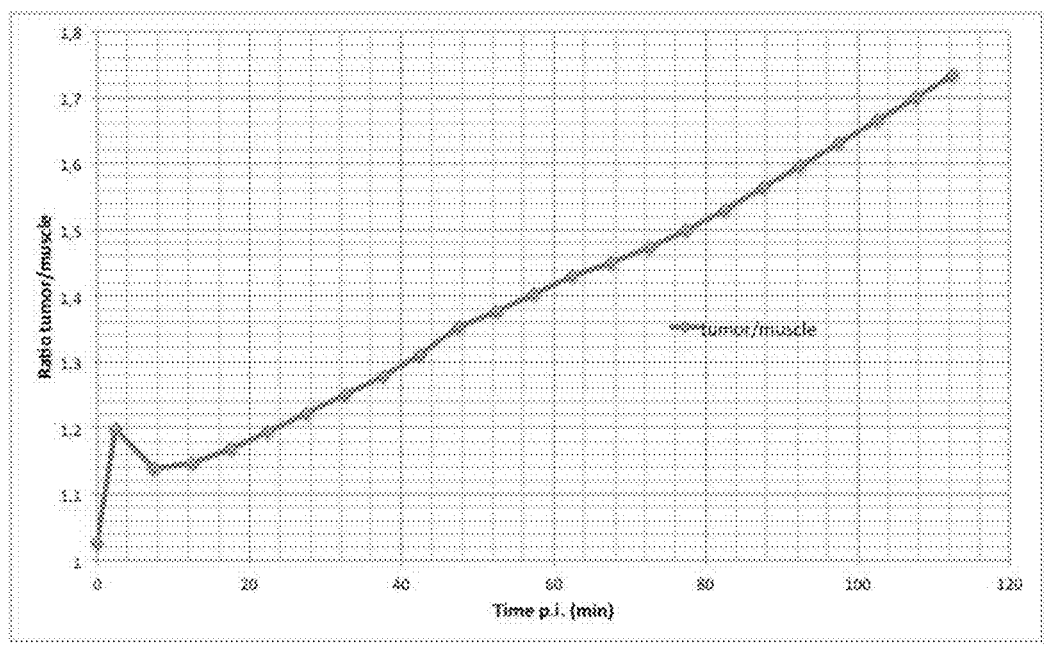
FIG. 9: Tumour to muscle ratio time curve of the fluorescence intensity kinetics in a NMRI nu/nu tumour (FaDu) bearing mouse.

A more detailed dynamic study of the fast distribution of the Kodak-XS-670-labeled nanoparticles in tumour bearing (FaDu) NMRI nu/nu mouse was carried out after single intravenous injection of 200 µL Kodak-XS-670-labeled nanoparticles. The 2D near infrared (NIR) fluorescence (excitation 670 nm, emission 790 nm, measurement duration of each frame 5 min) was measured before injection (0 min) and every 5 min up to 2 hours in the inhalation anesthetized (9% desflurane, 30% oxygen) mouse (body temperature 37° C.). The fluorescence intensity of different regions representing heart, tumour, muscle, intestine and bladder in the images (see FIG. 6) was measured by the ROVER software (ABX GmbH, Radeberg, Germany). Masks for defining two-dimensional regions of interest (ROI) were set and the ROI's were defined by threshold and ROI time activity curves (TAC) were derived for the subsequent data analysis. The fluorescence intensity (units/cm$^2$) and the normalized to the maximum value data were used for further analysis. The multiple frames (FIG. 7) show the fast accumulation of the nanoparticles in the bladder and the decreasing intensity in the thorax region. The fluorescence intensity after 2 h was highest in the bladder, followed by intestine, tumour, heart, and muscle. The kinetic analysis of the time-fluorescence curves (FIG. 8) showed clearance in all measured regions with half-lives of 24 min (thorax-heart), 22 min (muscle), 25 min (tumour). These fluorescence signals of the nanoparticle kinetics in the body are in good agreement with the quantitative measurements using small-animal PET (half life of $^{64}$Cu-labeled nanoparticles was in the muscle 18 min) if the measured regions are located near to the surface (skin). The similar values of the measured half-lives in the fluorescence measurements could be explained by the dominant effect of the Kodak-XS-670-labeled nanoparticles in the blood. It is noteworthy that the relation of the fluorescence intensity tumour to muscle shows a continuously increase over the time (FIG. 9).

Example 2: Preparation and In Vivo Characterization of $^{64}$Cu-Labeled Silicon Nanoparticles (DMPTACN-Containing Silicon Nanoparticles)

0.7 mg (1.4 µmol) 2-[4,7-Bis(pyridylmethyl)-1,4,7-triazacyclononan-1-yl]-N-(4-isothiocyanatophenyl)-acetamide (DMPTACN-Ph-NCS) as bifunctional chelating agent in 200 µL water was added to 0.5 mL amino-terminated silicon nanoparticles (c=2 mg/mL) dissolved in NaHCO$_3$ buffer (10 mM, pH=8.3). The mixture was stirred for 24 hours at room temperature. Purification of the DMPTACN-Ph-thiourea-containing silicon nanoparticles was performed using dialysis (MWCO 7000, SERVA, Membra-Cel). The dialysate was concentrated under reduced pressure. The residual was dissolved in 100 µL water/acetonitrile (1/1) and analyzed by HPLC. Dialysis was repeated five times with 500 mL H$_2$O each in 8 hours cycles. After that, DMPTACN-Ph-NCS was not detected by HPLC (Jupiter proteo 4 µm C12 90 Å (Phenomenex), 250×4.6 mm; eluent A (acetonitrile containing 0.1% trifluoroacetic acid, eluent B (water containing 0.1% trifluoroacetic acid, elution gradient 10% A to 100% in 60 minutes, 1 mL/min, $t_{R\ (DMPTACN\text{-}Ph\text{-}NCS)}$=20.6 min) The retentate was then concentrated under reduced pressure. DMPTACN-Ph-thiourea-containing silicon nanoparticles (100 µg in 160 µL) were dissolved in 2-[N-morpholino] ethanesulfonic acid (MES)-NaOH buffer (0.02 M, pH=6.2, c=625 µg nanoparticles/mL). For biodistribution and small animal PET experiments, 100 µg DMPTACN-Ph-thiourea-containing silicon nanoparticles dissolved in 250 µL MES-NaOH buffer were radiolabeled with [$^{64}$Cu]CuCl$_2$ (40 MBq in 0.01 HCl) at room temperature for 30 minutes. To remove the non-specific bound radioactivity, 10 µL aqueous solution of 10 mM TETA (1,4,8,11-tetraazacyclotetradecane-1,4,8,11-tetraacetic acid) was added to the radiolabeled silicon nanoparticles and incubated for 10 minutes at room temperature. Purification of $^{64}$Cu-labeled silicon nanoparticles was performed by HPLC (Jupiter proteo 4 µm C12 90 Å (Phenomenex), 250×4.6 mm; eluent A (acetonitrile containing 0.1% trifluoroacetic acid), eluent B (water containing 0.1% trifluoroacetic acid, elution gradient 10% A to 100% in 30 minutes, 1 mL/min, $t_{R\ (64Cu\text{-}TETA)}$=4.1 min, $t_{R\ (64Cu\text{-}DMPTACN\text{-}silicon\ nanoparticles)}$=12.3 min) Solvents used for HPLC were evaporated in vacuo, and after that the $^{64}$Cu-labeled silicon nanoparticles were dissolved in isotonic sodium chloride solution.

Figure 10:
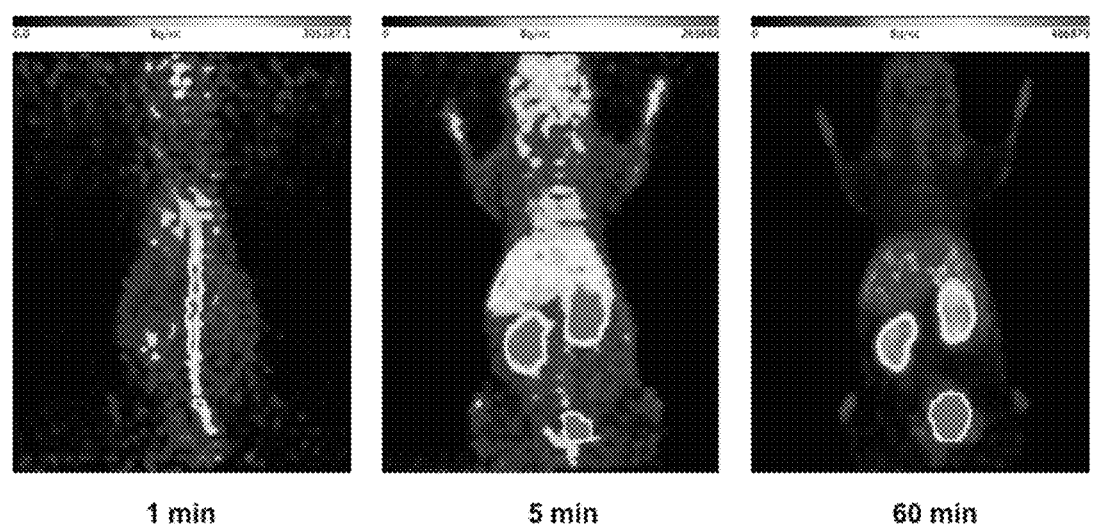
FIG. 10: Representative maximum intensity projections of small-animal PET images (1, 5 and 60 minutes) of NMRI nu/nu mouse using $^{64}$Cu-radiolabeled DMPTACN-containing silicon nanoparticles.
Figure 11:
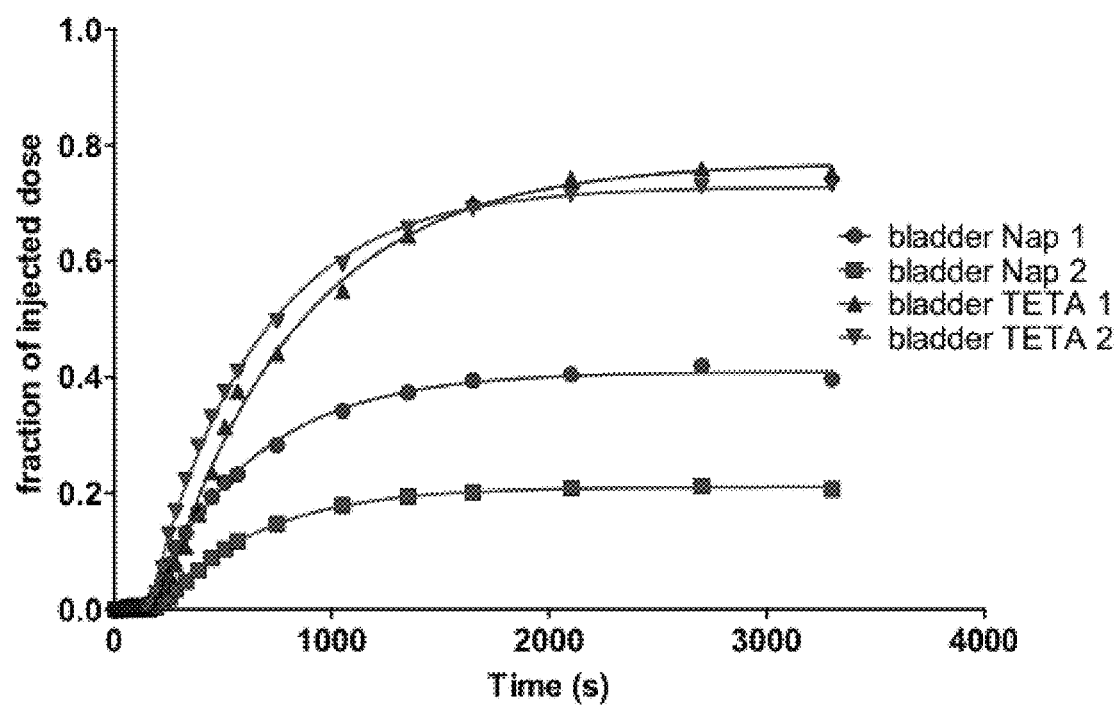
FIG. 11: Accumulation kinetics of $^{64}$Cu-labeled silicon nanoparticles (DMPTACN-containing silicon nanoparticles) (NAP 1—mouse 1, NAP 2—mouse 2) and $^{64}$Cu-TETA (TETA 1—mouse 3, TETA 2—mouse 4) for comparison in the bladder of four mice.

20 MBq of $^{64}$Cu-silicon nanoparticles in 0.5 mL isotonic NaCl solution was administered intravenously over one minute into the tail vein of a NMRI nu/nu mouse. The mice (body weight 40±3 g) were anesthetized through inhalation of Desflurane (10% Suprane) in 30% oxygen/air (gas flow, 1 L/min) Mice were positioned and immobilized prone with their medial axis parallel to the axial axis of the scanner (microPET® P4, Siemens preclinical solutions, Knoxville, Tenn., USA). For attenuation correction, a 10 min transmission scan was obtained using a rotating $^{57}$Co point source before tracer injection and collection of the emission scans. The radioactivity of the injection solution in 1 mL syringe was measured in the well counter cross-calibrated with the scanner. The emission scan of 120-min PET acquisition was started and with a delay of 30 s the infusion of the radiotracer was initiated. A solution of 0.5 mL isotonic solution of about 1 MBq/animal was infused over 1 min with a Harvard Apparatus 44 syringe pump (Harvard Apparatus, Holliston, Mass., USA) using a needle catheter into a tail vein. Data acquisition was performed in 3D list mode. Emission data were collected continuously. The list mode data were sorted into sinograms with 32 frames (15×10 s, 5×30 s, 5×60 s, 4×300 s, 3×600 s). The data were decay, scatter and attenuation corrected. The frames were reconstructed by Ordered Subset Expectation Maximization applied to 3D sinograms (OSEM3D) with 14 subsets, 15 OSEM3D iterations, 25 maximum a posteriori (MAP) iterations, and 1.8 mm resolution using the FastMAP algorithm (Siemens Preclinical Solutions, Knoxville, Tenn.). The pixel size was 0.07 by 0.07 by 0.12 cm, and the resolution in the center of field of view was 1.8 mm. No correction for partial volume and recovery effects was applied. The image volume data were converted to Siemens ECAT7 format for further processing. The image files were then processed using the ROVER software (ABX GmbH, Radeberg, Germany). Masks for defining three-dimensional regions of interest (ROI) were set and the ROI's were defined by thresholding and ROI time activity curves (TAC) were derived for the subsequent data analysis. The ROI data and TAC were further analyzed using R (R is available as Free Software under the terms of the Free Software Foundation's GNU General Public License in source code form) and especially developed program packages (Jörg van den Hoff, Helmholtz-Zentrum Dresden-Rossendorf, Dresden, Germany). The standardized uptake values ($SUV_{PET}$, $SUV_{PET}$=(activity/mL tissue)/(injected activity/body weight), mL/g; g/mL) and the fraction of injected activity were calculated in the ROIs. FIG. 10 shows the distribution of the $^{64}$Cu-DMPTACN-silicon nanoparticles at 1, 5, and 60 min after injection. The particles were fast distributed and eliminated from the blood by the kidneys. After one hour the main activity amounts are in the bladder (quantitative data shown in FIG. 11) and the kidneys. Altogether, biodistribution and pharmacokinetics of $^{64}$Cu-DMPTACN-silicon nanoparticles are very similar to the $^{64}$Cu-labeled hydrophilic chelator TETA (1,4,8,11-tetraazacyclotetradecane-1,4,8,11-tetraacetic acid).

Example 3: Preparation and In Vivo Characterization of $^{64}$Cu-Labeled Silicon Nanoparticles NOTA-Containing Silicon Nanoparticles)

1 mg (1.8 μmol) S-2-(4-Isothiocyanatobenzyl)-1,4,7-triazacyclononane-1,4,7-triacetic acid (SCN-Bn-NOTA) as bifunctional chelating agent was added to 0.5 mL aminoterminated silicon nanoparticles (c=2 mg/mL) dissolved in a borate buffer (0.1 M, pH=9.2). The mixture was stirred for 24 hours at room temperature. Purification of the NOTA-containing silicon nanoparticles was performed using dialysis (Pierce Slide A-Lyzer Cassette (MWCO=7000 g/mol), 2×PBS 400 mL, 1×H$_2$O 400 mL). The dialysate was concentrated under reduced pressure. The residual was dissolved in 100 μL, water/acetonitrile (1/1) and analyzed by HPLC. After purification by ultracentrifugation, SCN-Bn-NOTA was not detected by HPLC (ZORBAX 300 Extend-C18 5 μm, 4.6×250 mm; eluent A (H$_2$O containing 0.1% trifluoroacetic acid), eluent B (acetonitrile containing 0.1% trifluoroacetic acid, elution gradient 90% A to 10% in 20 minutes, 1 mL/min, $t_{R\ (SCN-Bn-NOTA)}$=13.697 min) The retentate was concentrated under reduced pressure. NOTA-thiourea-containing silicon nanoparticles were dissolved in 2-[N-morpholino]ethanesulfonic acid (MES)-NaOH buffer (0.05 M, pH=5.5, c=400 μg nanoparticles/mL). For biodistribution and small animal PET experiments, 100 μg DMP-TACN-Ph-thiourea-containing silicon nanoparticles dissolved in 250 μL, MES-NaOH buffer were radiolabeled with [$^{64}$Cu]CuCl$_2$ (40 MBq in 0.01 HCl) at room temperature for 30 minutes. At the end of the reaction, 10 μL, aqueous solution of 10 mM TETA (1,4,8,11-tetraazacyclotetradecane-1,4,811-tetraacetic acid) was added to the radiolabeled silicon nanoparticles and incubate for 10 minutes at room temperature to remove the non-specific bound radioactivity. (ZORBAX 300 Extend-C18 5 μm, 4.6×250 mm; eluent A (H$_2$O containing 0.1% trifluoroacetic acid), eluent B (acetonitrile containing 0.1% trifluoroacetic acid, elution gradient 90% A to 10% in 20 minutes, 1 mL/min, $t_R$ ($^{64}$Cu-NOTA-silicon nanoparticles)=11.72 min). Solvents used for HPLC were evaporated in vacuo, and the $^{64}$Cu-labeled silicon nanoparticles were dissolved in isotonic sodium chloride solution. 20 MBq of $^{64}$Cu-NOTA-silicon nanoparticles in 0.5 mL isotonic NaCl solution was administered intravenously over one min into a tail vein of a NMRI nu/nu mouse. Biodistribution and pharmacokinetics of $^{64}$Cu-NOTA-silicon nanoparticles are comparable to those of $^{64}$Cu-DMPTACN-silicon nanoparticles.

Example 4: Preparation and In Vivo Characterization of $^{90}$Y-Labeled Silicon Nanoparticles (DOTA-Containing Silicon Nanoparticles)

40 μL (291 μg, 0.4 μmol) (S)-2-(4-Aminobenzyl)-1,4,7,10-tetraazacyclododecane-N,N',N'',N'''-tetraacetic acid (NH$_2$-Bn-DOTA) was dissolved in 1 mL 0.5 M NH$_4$OAc buffer (pH=6.8). Then, 30 μL [$^{90}$Y]YCl$_3$ (120 MBq) in 0.04 HCl was added, and the solution was stirred for 20 min at 95° C. in a thermo-mixer (1000 rpm). Purification of $^{90}$Y-labeled NH$_2$-Bn-DOTA was performed by means of SepPak Plus C$_{18}$ cartridge (Waters, USA). After separation of unbound $^{90}$Y$^{3+}$ with 10 mL of NH$_4$OAc buffer (pH=6.5, 0.05 M), [$^{90}$Y]Y—NH$_2$-Bn-DOTA was selectively eluted with 1.5 mL acetonitrile/water (80/20 v/v). The solution was evaporated to dryness under a nitrogen stream. The residue was dissolved in 100 μL MES-NaOH buffer, and the purity of was checked by Radio-HPLC (Phenomenex Aqua-C18, 5 μm, 4.6×250 mm; eluent: 50 mM NH$_4$OAc in water/acetonitrile=95/5, isocratic elution, 1 mL/min, ($^{90}$Y$^{III}$, $t_R$=3.8 min; [$^{90}$Y]Y—NH$_2$-Bn-DOTA-isomer 1, $t_R$=9.1 min; [$^{90}$Y]Y—NH$_2$-Bn-DOTA-isomer 2, $t_R$=11.9 min; isomers according to Schlesinger et al.: Bioconjugate Chem. 2008; 19:928-39) and Radio-TLC (50 mM NH$_4$OAc in water/acetonitrile=90/10 on silica plates ([$^{90}$Y]YCl$_3$, R$_f$=0; [$^{90}$Y]Y—NH$_2$-Bn-DOTA, R$_f$=0.7). A radiochemical yield higher than 99% was determined using Radio-HPLC.

To 100 μg carboxylic acid-terminated silicon nanoparticles dissolved in 150 μL MES-NaOH buffer (pH=5.5), 1 mg 1-ethyl-3-(3-dimethylaminopropyl) carbodiimide hydrochloride (EDC) was added and the mixture was incubated in a thermo mixer for ten minutes at room temperature. To this solution, 100 MBq [$^{90}$Y]Y—NH$_2$-Bn-DOTA was added and the mixture was stirred for three hours at room temperature. Purification of the $^{90}$Y-labeled DOTA-containing silicon nanoparticles was performed using dialysis (Pierce Slide A-Lyzer Cassette (MWCO=7000 g/mol), 2×PBS 400 mL, 1×H$_2$O 400 mL). The dialysate was concentrated under reduced pressure. The residual was dissolved in 100 μL MES-NaOH buffer and analyzed by HPLC. After purification by ultracentrifugation, no free [$^{90}$Y]Y—NH$_2$-Bn-DOTA was detected by Radio-HPLC. Solvents were evaporated using a nitrogen stream, and the $^{90}$Y-labeled silicon nanoparticles were dissolved in isotonic sodium chloride solution. In vivo investigations were performed with $^{90}$Y-labeled silicon nanoparticles dissolved in in isotonic sodium chloride solution with a specific activity of 10 to 200 MBq/μg silicon nanoparticles.

Animal cohorts: Tumorigenic human cancer cells like human squamous cell carcinoma cells or prostate carcinoma cells were implanted subcutaneously into the leg or neck regions or human brain carcinoma cells by using stereotactic procedures into the brains of a number of athymic nude mice and allowed to develop into a tumor for 8 to 24 days. Mice with tumors ranging from 6 to 12 mm in diameter (approximately 1 cm$^3$ in volume) were selected for the studies. $^{90}$Y-labeled DOTA-containing silicon nanoparticles (0.5 to 5 MBq) in approximately 0.2 ml were applied in the studies.

Biodistribution: Biodistribution studies with $^{90}$Y-labeled DOTA-containing silicon nanoparticles were performed in mice at various time points over 3 weeks using SPECT, section or autoradiography to evaluate $^{90}$Y-content. Radionuclide imaging was performed using small animal SPECT/CT at each time point immediately followed by euthanasia.

For anatomical localization of SPECT images, X-ray CT data were acquired; volumetric CT images were reconstructed provided by an algorithm the manufacturer. Following euthanasia, major organs including heart, lungs, brain, liver, pancreas, kidneys, small intestine, and intestine were isolated, the tumor was resected, and samples of bone (femur), skin, and muscle were dissected. These samples were weighed and counted with appropriate standards using a calibrated gamma scintillation counter or the samples were dissolved in tissue solubilzer and bleached with hydrogen peroxide and perchlorate followed by addition of scintillator and counted in scintillation counter to determine the localization of the specific radiolabeled nanoparticles in each organ. The results of scintillation counting were expressed as percentage of the injected dose per gram of tissue (% ID/g) or SUV (g/mL) and were corrected for physical radionuclide decay. To determine differences in the biodistribution of the $^{90}$Y-nanoparticles, statistical analysis (Student's t test) was performed using SPSS 11 software package (SPSS, Chicago, Ill., USA).

Autoradiography: Tumor tissue samples were immediately frozen at −60° C. and embedded in tissue medium. Tissue samples were cryosectioned at 20-μm thicknesses. Sections were mounted on glass coverslips, placed on cardboard, and exposed on a storage phosphor image plate for 1 to 12 h. The plate then was scanned with an imaging system.

Survival studies: Survival studies involved minimal three cohorts mice that received $^{90}$Y-DOTA or the non-labeled nanoparticles or the radiolabeled $^{90}$Y-labeled DOTA-containing silicon nanoparticles by intravenous infusion or intraperitoneal injection or by means of convection enhanced delivery into the brains at one to three weeks after tumor implantation. Mice in survival studies were divided into three groups: one comprised untreated mice that received the non-labeled nanoparticles, the $^{90}$Y-DOTA and the other comprised mice treated with the $^{90}$Y-labeled DOTA-containing silicon nanoparticles that received between 20 and 60 MBq of $^{90}$Y-labeled DOTA-containing silicon nanoparticles. Survival data were evaluated by using Kaplan-Meier statistical methods.

Example 5: Preparation and In Vivo Characterization of $^{177}$Lu-Labeled Silicon Nanoparticles (DOTA-Containing Silicon Nanoparticles)

$^{177}$Lu-labeled silicon nanoparticles have been obtained using the same procedure applied for the $^{90}$Y-labeling described in example 4. In vivo investigations were performed with $^{177}$Lu-labeled silicon nanoparticles dissolved in in isotonic sodium chloride solution with a specific activity of 10 to 200 MBq/μg silicon nanoparticles.

Animal cohorts: Tumorigenic human cancer cells like human squamous cell carcinoma cells or prostate carcinoma cells were implanted subcutaneously into the leg or neck regions or human brain carcinoma cells by using stereotactic procedures into the brains of a number of athymic nude mice and allowed to develop into a tumor for 8 to 24 days. Mice with tumors ranging from 6 to 12 mm in diameter (approximately 1 cm3 in volume) were selected for the studies. $^{177}$Lu (40±20 MBq) in approximately 0.2 ml were applied in the studies.

Biodistribution: Biodistribution studies with $^{177}$Lu-labeled particles were performed in mice at various time points over 3 weeks using SPECT, section or autoradiography to evaluate 177Lu-content. Radionuclide imaging was performed using small animal SPECT/CT at each time point immediately followed by euthanasia.

For anatomical localization of SPECT images, X-ray CT data were acquired; volumetric CT images were reconstructed provided by an algorithm the manufacturer. Following euthanasia, major organs including heart, lungs, brain, liver, pancreas, kidneys, small intestine, and intestine were isolated, the tumor was resected, and samples of bone (femur), skin, and muscle were dissected. These samples were weighed and counted with appropriate standards using a calibrated gamma scintillation counter to determine the localization of the specific radiolabeled nanoparticles in each organ. The results of scintillation counting were expressed as percentage of the injected dose per gram of tissue (% ID/g) or SUV (g/mL) and were corrected for physical radionuclide decay. To determine differences in the biodistributions of the $^{177}$Lu-nanoparticles statistical analysis (Student's t test) was performed using SPSS 11 software package (SPSS, Chicago, Ill., USA).

Autoradiography: Tumor tissue samples were immediately frozen at −60° C. and embedded in tissue medium. Tissue samples were cryosectioned at 20-μm thicknesses. Sections were mounted on glass coverslips, placed on cardboard, and exposed on a storage phosphor image plate for 1 to 12 h. The plate then was scanned with an imaging system.

Survival studies: Survival studies involved minimal three cohorts mice that received $^{177}$Lu-DOTA or the non-labeled nanoparticles or the radiolabeled $^{177}$Lu-nanoparticles by intravenous infusion or intraperitoneal injection or by means of convection enhanced delivery into the brains at one to three weeks after tumor implantation. Mice in survival studies were divided into three groups: one comprised untreated mice that received the non-labeled nanoparticles, the $^{177}$Lu-complex and the other comprised mice treated with the $^{177}$Lu-labeled nanoparticles that received between 20 and 60 MBq of $^{177}$Lu-nanoparticles. Survival data were evaluated by using Kaplan-Meier statistical methods.

Example 6: Preparation of Peptide-Conjugated Silicon Nanoparticles and Targeting to Epidermal-Growth-Factor-Receptor (EGFR)

To 0.5 mg amino-terminated silicon nanoparticles, dissolved 100 μL, PBS buffer, 137 μg (11 μmol) 2-iminothiolane hydrochloride was added, and the mixture was stirred for 12 hours at room temperature. A maleimido-functionalized peptide conjugate was obtained by treatment of 0.5 μmol gly-gly-gly-leu-ala-arg-leu-leu-thr with 0.55 μmol 3-(maleimido) propionic acid N-succinimidyl ester in 100 μL, PBS buffer for 12 hours at room temperature. A maleimido-functionalized dye molecule was prepared by reaction of 0.15 μmol 8-(3-Aminopropyl)-4,4-difluoro-1,3,5,7-tetramethyl-4-bora3a,4a-s-indacene (BODIPY-NH$_2$) with 0.15 μmol 3-(maleimido) propionic acid N-succinimidyl ester in 500 μL, PBS buffer for 12 hours at room temperature. The three reaction products (sulfydryl-terminated silicon nanoparticles, maleimido-functionalized peptide and dye conjugate) were mixed together and stirred 15 hours at room temperature. The reaction product was filtered three times using a membrane filter (Amicon Ultra—0.5 ml 3 K, Amicon Ultra centrifugal filters, MILLIPORE) with PBS buffer at 6000 rpm. For saturation of the remaining sulfhydryl groups, the purified silicon nanoparticles were re-suspended in 100 μL, PBS buffer, and 7 μmol of 25-maleinimido-23-oxo-4,7,10,13,16,19-hexaoxa-22-azapentacosanoic acid succinimidyl ester was added. The reaction mixture was stirred for 8 hours at room temperature. The pegylated particles were purified three times using a membrane filter (Amicon Ultra—0.5 ml 3 K, Amicon Ultra centrifugal filters, MILLIPORE) with deionized water at 6000 rpm.

Targeting to Epidermal-Growth-Factor-Receptor (EGFR) of the pegylated silicon nanoparticles containing peptide residues (5% gly-gly-gly-leu-ala-arg-leu-leu-thr) and the fluorescent tag BODIPY (1%) was proven by an immunological binding assay. A human epithelial carcinoma cell line (A431) growing under appropriate conditions was harvested and lysed by mechanical disruption in phosphate-buffered-saline (PBS) including 0.05% Chremophor®. This detergent was suitable for solubilisation of membrane proteins, which were obtained in the supernatant after centrifugation of the lysed cells. Protein content was determined by Bradford's method (Bradford, Anal. Biochem. 1976, 72, 248-254). Different concentrations of pegylated silicon nanoparticles with gly-gly-gly-leu-ala-arg-leu-leu-thr) and BODIPY were added to definitive protein concentrations of the supernatant in PBS buffer and allowed to react for 30 minutes at 37° C. The reaction was stopped by addition of Laemmli sample buffer and proteins were separated subsequently by sodium dodecylsulfate-polyacrylamide gel electrophoresis (SDS-PAGE) (Laemmli, Nature 1970, 227, 680-685). Proteins were transferred from the gel onto nitrocellulose membrane by semi-dry electro-blotting at 4° C. overnight. Fluorescent protein bands on the membrane were detected by an imaging system using excitation/emission wavelengths of 488/520 nm. After blocking, the membrane was incubated with an anti-EGFR antibody and subsequently with a secondary, horseradish-peroxidase labeled antibody. EGFR bands were detected using the peroxidase reaction producing chemiluminescence. The exact alignment of the fluorescence (BODIPY) and chemiluminescence in one protein band suggest a stable bound between the silicon nanoparticle-peptide conjugate and EGFR even under reducing conditions during a SDS gel electrophoresis.

The invention claimed is:

1. A silicon nanoparticles characterised in that they comprise a bioinert silicon core of a size of 1 to 10 nm and are terminated with allylamine or poly(allylamine) comprising up to 10 allylamine groups, wherein
   a. the nanoparticle's surface is mono-functionalised or multi-functionalised with a functional group visualizable using X-ray, MRI, ultrasound or microwave, or optical imaging involving luminescence or fluorescence, CT, PET, or SPECT; and
   b. the functionalized group is selected from the group comprising a luminescent compound, a fluorescent compound, a light absorbing compound, a radioactive compound, a metal compound that can be visualized using x-rays, a compound that can be visualized using magnetic resonance imaging (MRI), a compound that can be visualized using ultrasound or microwave, a luminescent/fluorescent material that can be utilized in optical imaging, an X-ray contrast-giving agent that can be imaged by computed tomography (CT) and an isotope that can be imaged by positron emission tomography (PET) or single photon emission computed tomography (SPECT); and
   c. the nanoparticle's surface is bound to targeting molecules and/or therapeutically relevant molecules selected from the group comprising toxins, radionuclides and chemotherapeutics.

2. The silicon nanoparticles according to claim 1, wherein the X-ray contrast-giving agent comprises, iodinated compounds or gadolinium based compounds.

3. The silicon nanoparticles according to claim 1, wherein the nanoparticles are coated with at least one of proteins, lipids, surfactants, perfluoropropane or sulphur hexafluoride.

4. The silicon nanoparticles according to claim 1, wherein the contrast-giving material comprises at least one paramagnetic material selected from the group comprising rare earth, gadolinium, manganese, iron and copper complexes.

5. The silicon nanoparticles according to claim 1, wherein the contrast-giving agent for X-ray computed tomography comprises barium salts and/or polyoxometalates.

6. The silicon nanoparticles according to claim 1, wherein the isotopes that can be imaged by positron emission tomography are selected from the group comprising $^{64}$Cu, $^{68}$Ga, $^{86}$Y, $^{89}$Zr, $^{110}$In or $^{18}$F based tracer.

7. The silicon nanoparticles according to one of claim 1, wherein the isotopes that can be imaged by single photon emission computed tomography are selected from the group comprising $^{67}$Ga, $^{99m}$Tc, $^{111}$In or $^{201}$Tl.

8. The silicon nanoparticles according to claim 1, comprising at least one biomolecule selected from the group comprising a peptide, a protein, a sugar molecule, a nucleic acid or nucleic acid analogue bound to the nanoparticle.

9. The silicon nanoparticle according to claim 8, wherein the protein is an antigen, an antibody, a receptor or a ligand.

10. The silicon nanoparticles according to claim 1, wherein a pharmaceutically active compound is bound to the nanoparticle.

11. A pharmaceutical composition comprising silicon nanoparticles according to claim 1 and a pharmaceutically suitable carrier.

12. A method for synthesis of the silicon nanoparticles according to claim 1, said method comprising the steps of:
   mixing a surfactant and a solvent and sonification of the mixture for forming micelles,
   adding $SiCl_4$ and sonification,
   adding a reducing agent for forming hydrogen-terminated silicon nanoparticles and sonification,
   adding an allylamine or poly(allylamine) comprising up to 10 allylamine groups in the presence of a catalyst and sonification, and
   extracting and purifying the resulting silicon nanoparticles, and
   mono- or multi-functionalising the silicon nanoparticles surface with a functional group selected from the group comprising a luminescent compound, a fluorescent compound,
   a light absorbing compound, a radioactive compound, a metal compound that can be visualized using x-rays, a compound that can be visualized using magnetic resonance imaging (MRI), a compound that can be visualized using ultrasound or microwave, a luminescent/fluorescent material that can be utilized in optical imaging, a X-ray contrast-giving agent that can be imaged by computed tomography (CT) or an isotope that can be imaged by positron emission tomography (PET) or single photon emission computed tomography (SPECT); and
   binding the silicon nanoparticle's surface to targeting molecules and/or therapeutically relevant molecules selected from the group comprising toxins, radionuclides and chemotherapeutics.

13. The method according to claim 12, wherein the sonification in each case is performed simultaneously or subsequently.

14. The method according to claim 12, wherein the surfactant is tetraoctylammonium bromide, the solvent is toluene, the reducing agent is $LiAlH_4$ and the catalyst is $H_2PtCl_6$.

15. A method comprising the step of providing silicon nanoparticles of claim 1 for in vivo bioimaging.

16. A method comprising the step of providing a pharmaceutical composition according to claim 11 for in vivo bioimaging.

17. The method of claim 15, wherein in vivo bioimaging is used for in vivo diagnostics, visualization or staining of drug delivery, cells, biological processes or pathways.

18. A method comprising the step of providing silicon nanoparticles according to claim 1.

19. The method according to claim 18, wherein the chemotherapeutic agent comprises cisplatin, carboplatin, fluorouracil, methotrexate, paclitaxel, docetaxel or doxorubicin.

20. The method according to claim 18, wherein a radiometal complex is used comprising therapeutically relevant radionuclides selected from the group of $_{67}Cu$, $_{90}Y$, $_{131}I$, $_{153}SM$, $_{166}Ho$, $_{177}Lu$, $_{186}Re$ or $_{188}Re$.

21. A method comprising the step of providing silicon nanoparticles according to claim 1 for the combination of molecular in vivo imaging and targeted treatment of diseases.

22. A method comprising the step of providing silicon nanoparticles according to claim 1 in a combination of therapeutic methods selected from the group comprising hyperthermia, chemotherapy, radiation therapy and/or radionuclide therapy using targeted silicon nanoparticles.

* * * * *